(12) United States Patent
Tamezane et al.

(10) Patent No.: US 9,857,388 B2
(45) Date of Patent: Jan. 2, 2018

(54) AUTOMATIC ANALYZER

(71) Applicant: HITACHI HIGH-TECHNOLOGIES CORPORATION, Tokyo (JP)

(72) Inventors: Hideto Tamezane, Tokyo (JP); Isao Yamazaki, Tokyo (JP); Masaharu Nishida, Tokyo (JP); Kumiko Kamihara, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/763,225

(22) PCT Filed: Jan. 27, 2014

(86) PCT No.: PCT/JP2014/051723
§ 371 (c)(1),
(2) Date: Jul. 24, 2015

(87) PCT Pub. No.: WO2014/119525
PCT Pub. Date: Aug. 7, 2014

(65) Prior Publication Data
US 2015/0362514 A1 Dec. 17, 2015

(30) Foreign Application Priority Data
Jan. 31, 2013 (JP) .................. 2013-017095

(51) Int. Cl.
*G01N 35/00* (2006.01)
*G01N 35/10* (2006.01)

(52) U.S. Cl.
CPC . *G01N 35/00623* (2013.01); *G01N 35/00871* (2013.01); *G01N 35/1002* (2013.01);
(Continued)

(58) Field of Classification Search
None
See application file for complete search history.

(56) References Cited

U.S. PATENT DOCUMENTS

2004/0034479 A1 2/2004 Shimase
2008/0236301 A1 10/2008 Fukushima et al.
(Continued)

FOREIGN PATENT DOCUMENTS

EP 2 031 403 A1 3/2009
JP 2004-125780 A 4/2004
(Continued)

OTHER PUBLICATIONS

International Preliminary Report on Patentability received in corresponding International Application No. PCT/JP2014/051723 dated Aug. 13, 2015.
(Continued)

*Primary Examiner* — Jill Warden
*Assistant Examiner* — Benjamin R Whatley
(74) *Attorney, Agent, or Firm* — Mattingly & Malur, PC

(57) ABSTRACT

The dispensing mechanisms dips a dispensing nozzle in a dispensing target contained in a container 11, 21, and 31, aspirates the dispensing target, and discharges the dispensing target to a reaction container 41. One item of determination-purpose reference data is selected from multiple items of the determination-purpose reference data which is stored in a storage unit 93 and used in determining whether or not the dispensing mechanisms 50, 60, and 70 are abnormal, based on the detection result from a pressure sensor 54 when the dispensing mechanisms 50, 60, and 70 dispense a reference dispensing target configured to contain a known ingredient; and whether or not the dispensing mechanisms 50, 60, and 70 are abnormal is determined, based on the detection result from the pressure sensor 54 and the selected determination-purpose reference data when the dispensing mechanisms 50, 60, and 70 dispense a dispensing target used in analysis.

3 Claims, 7 Drawing Sheets

(52) U.S. Cl.
CPC ............... *G01N 35/1016* (2013.01); *G01N 2035/00633* (2013.01)

(56) References Cited

U.S. PATENT DOCUMENTS

2009/0070049 A1* 3/2009 Ziegler .............. G01N 35/1016
                                                    702/50
2010/0313687 A1* 12/2010 Ogusu ................ B01F 11/0071
                                                   73/864.11

FOREIGN PATENT DOCUMENTS

| | | |
|---|---|---|
| JP | 2004-271266 A | 9/2004 |
| JP | 3119773 U | 3/2006 |
| JP | 2006-343243 A | 12/2006 |
| JP | 2008-224691 A | 9/2008 |

OTHER PUBLICATIONS

International Search Report of PCT/JP2014/051723.
Japanese Office Action received in corresponding Japanese Application No. 2013-017095 dated Oct. 11, 2016.
Extended European Search Report received in corresponding European Application No. 14745549.7 dated Aug. 19, 2016.

* cited by examiner

[Fig. 1]
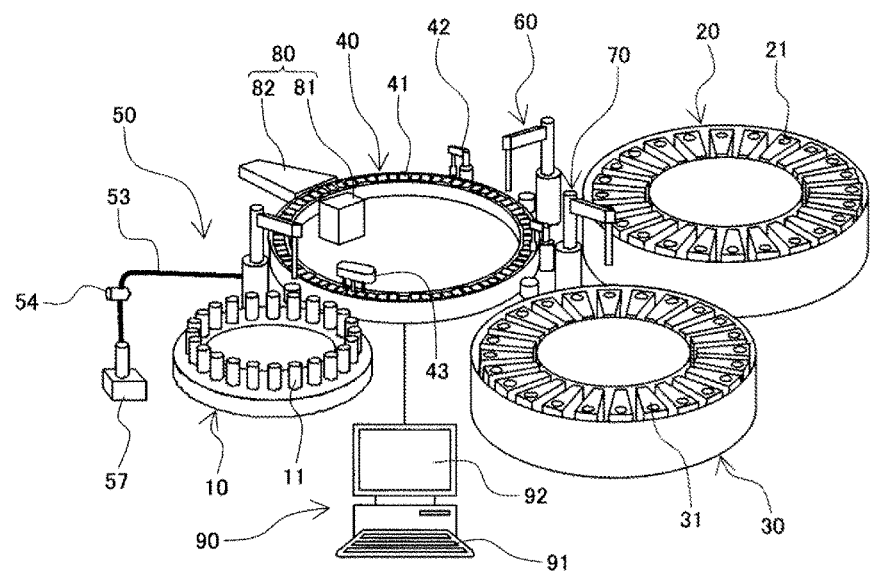
[Fig. 2]
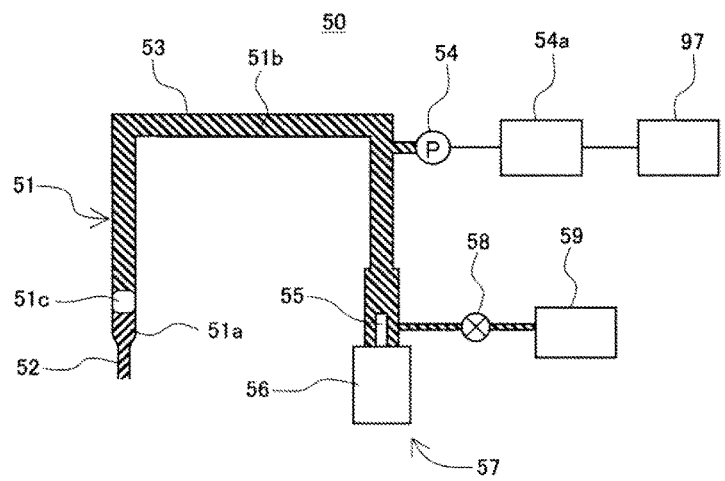

[Fig. 3]
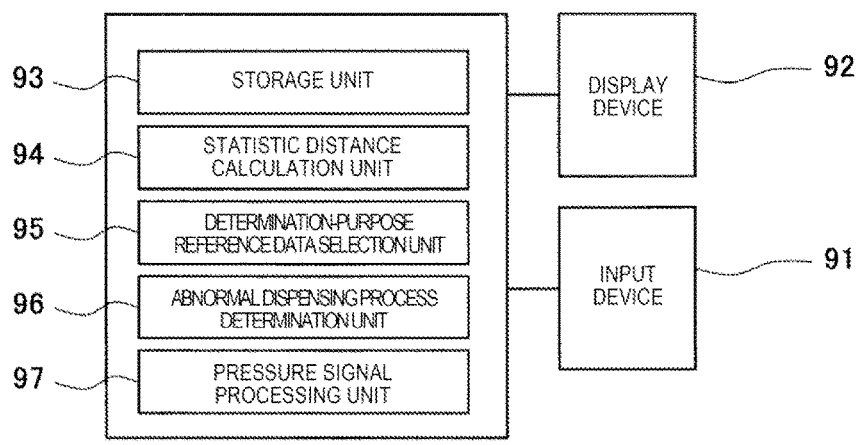
[Fig. 4]
| NO. OF FEATURE VARIABLES / NO. OF EVENTS | 1 | 2 | ... | k−1 | k |
|---|---|---|---|---|---|
| 1 | $X_{11}$ | $X_{12}$ | ... | $X_{1,k-1}$ | $X_{1k}$ |
| 2 | $X_{21}$ | $X_{22}$ | ... | $X_{2,k-1}$ | $X_{2k}$ |
| ⋮ | ... | ... | ... | ... | ... |
| n−1 | $X_{n-1,1}$ | $X_{n-1,2}$ | ... | $X_{n-1,k-1}$ | $X_{n-1,k}$ |
| n | $X_{n1}$ | $X_{n2}$ | ... | $X_{n,k-1}$ | $X_{nk}$ |

[Fig. 5]
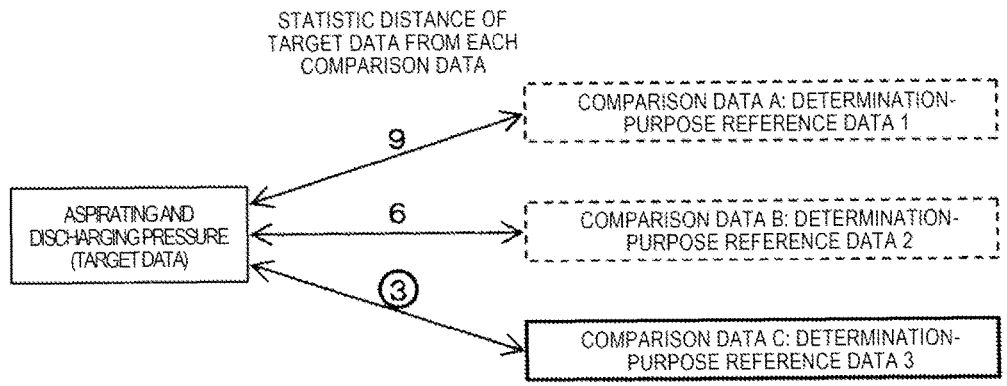
[Fig. 6]
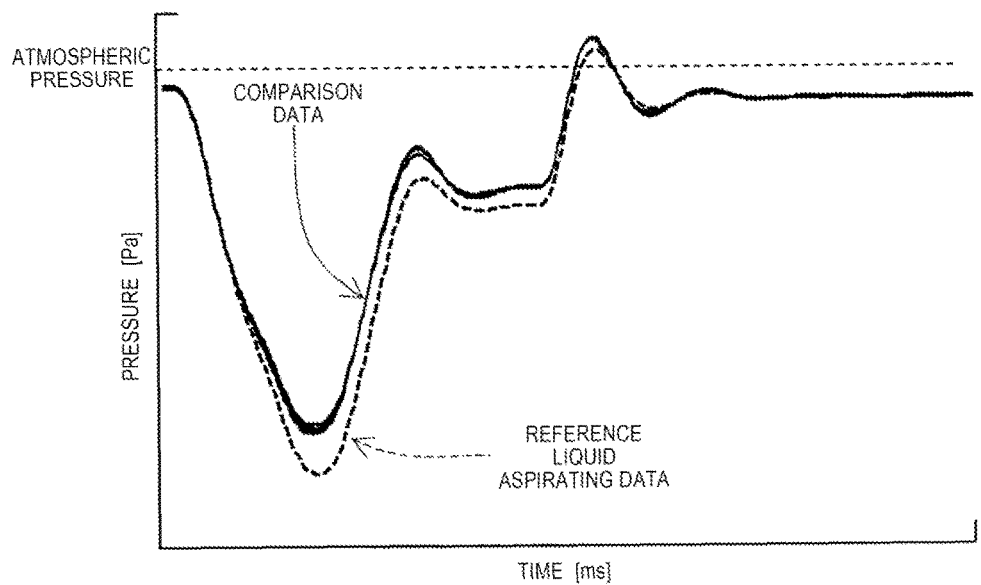

[Fig. 7]
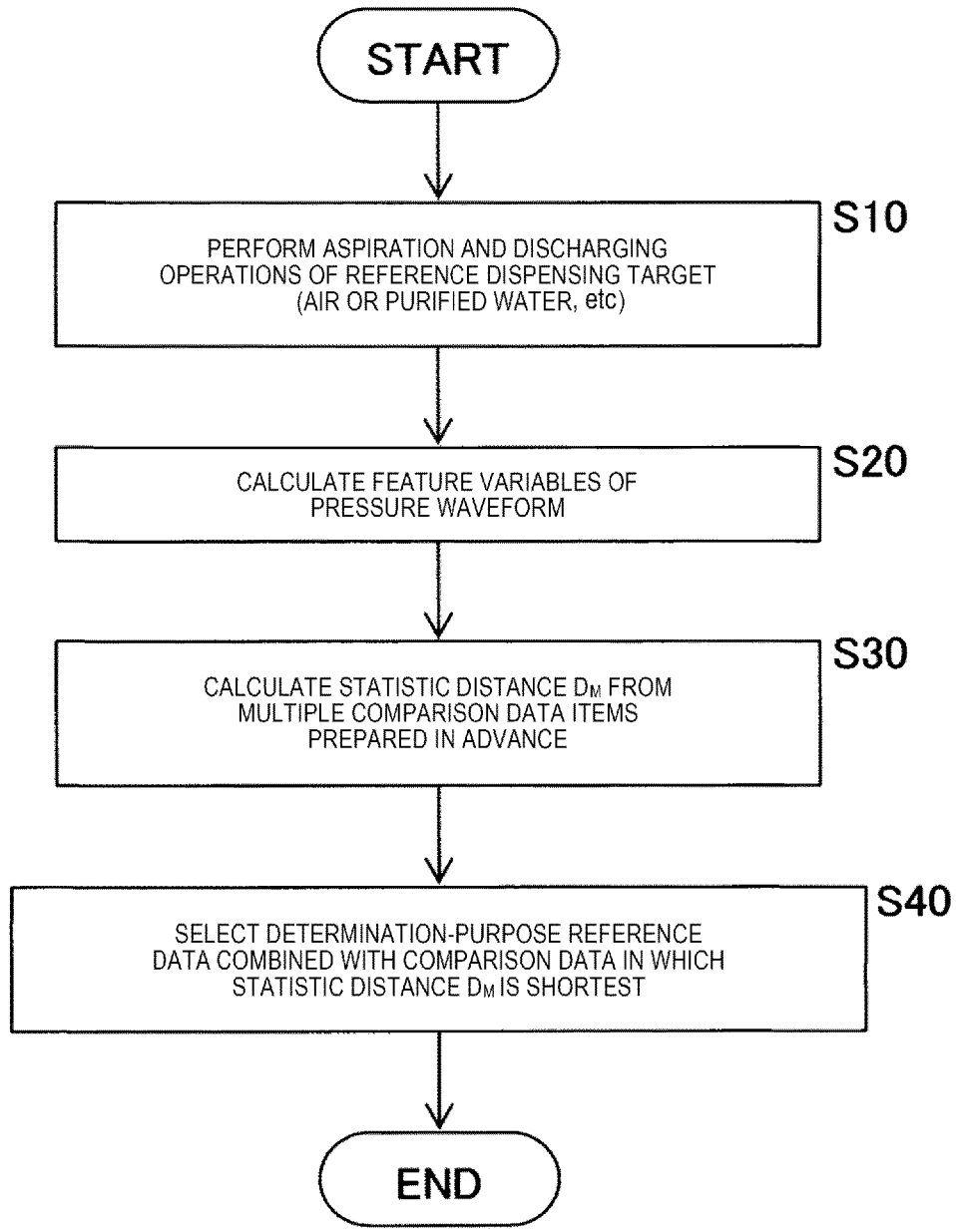

[Fig. 8]
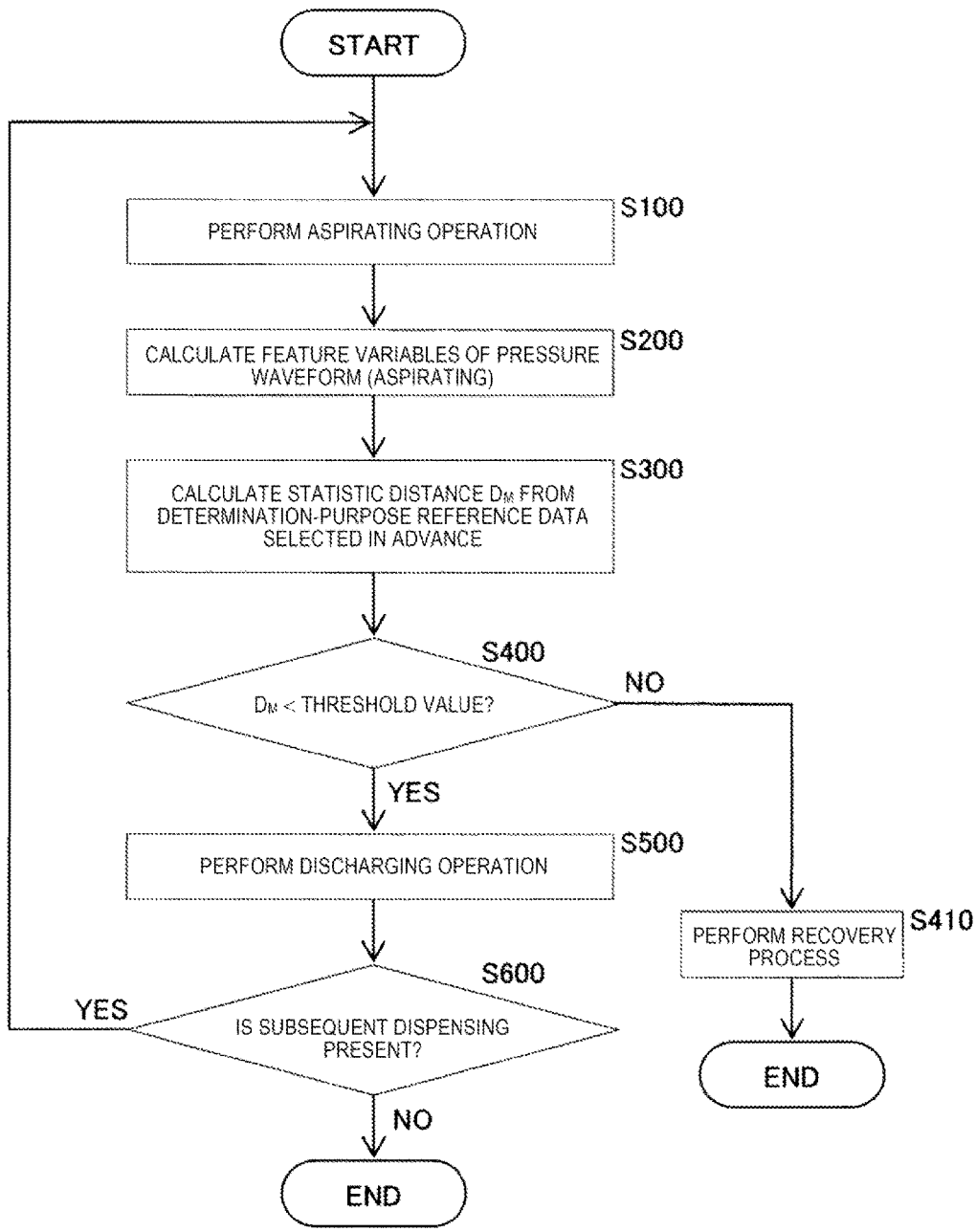

[Fig. 9]
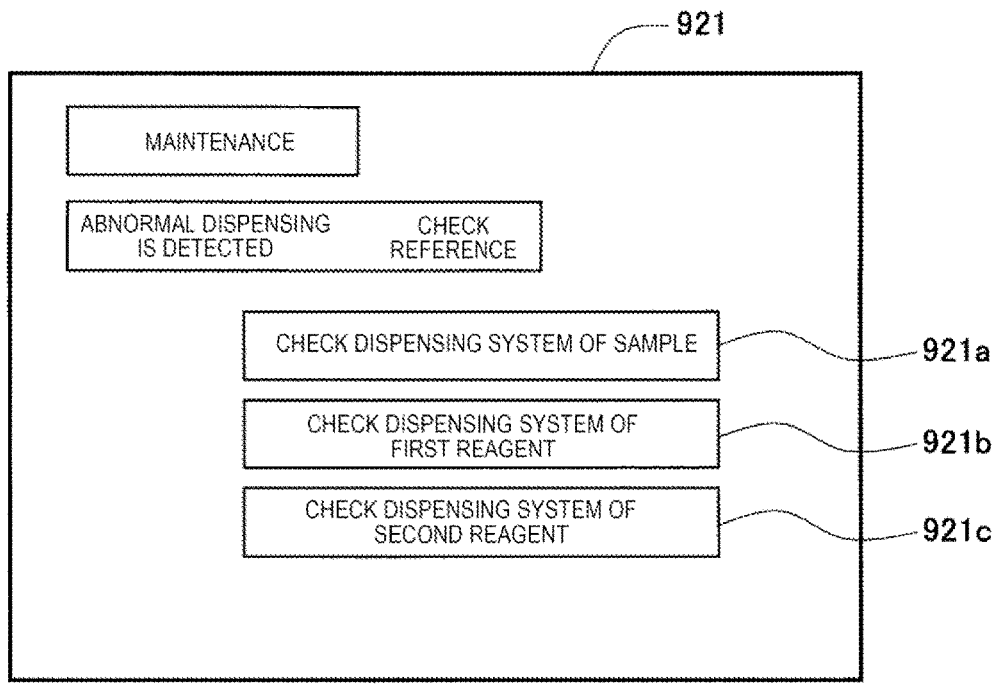
[Fig. 10]
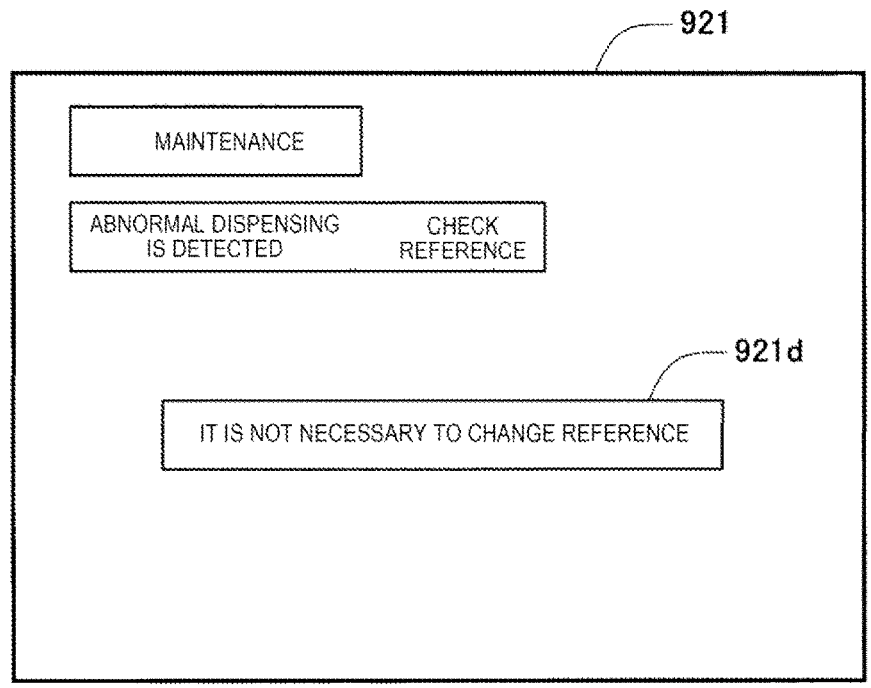

[Fig. 11]
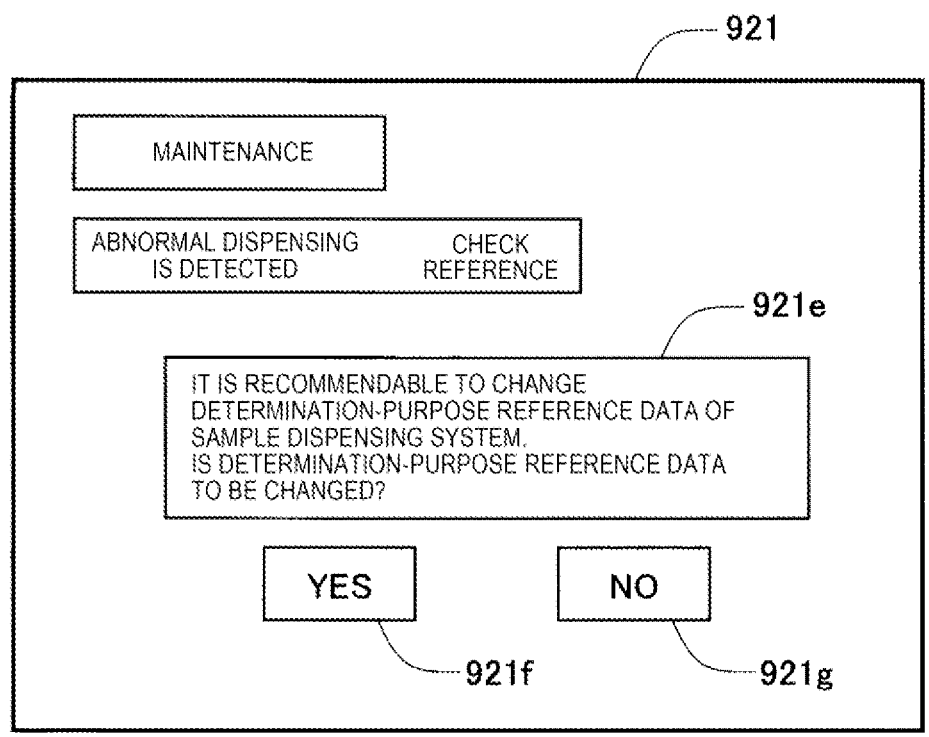

AUTOMATIC ANALYZER

TECHNICAL FIELD

The present invention relates to an automatic analyzer which performs qualitative/quantitative analysis on a living body specimen such as blood or urine.

BACKGROUND ART

An automatic analyzer performs qualitative/quantitative analysis by adding a reagent specifically reacting to a specific ingredient contained in a living body specimen (hereinafter, referred to as a specimen) such as blood or urine, by causing the reagent to react therewith, and by measuring optical density or an emitted light quantity of reaction liquid.

According to this automatic analyzer, in order to cause the specimen and the reagent to react with each other, it is necessary to provide a step of dispensing the specimen which is an analysis target contained in a specimen container or the reagent which is added to and reacted with the specimen, into a reaction container. A small amount of the specimen or the reagent is dispensed into the reaction container. Accordingly, accurate dispensing inevitably affects accurate analysis. Therefore, it is important to reliably detect abnormal dispensing which may lead to inaccurate dispensing.

For example, as a technique of detecting abnormal dispensing, PTL 1 (JP-A-2008-224691) discloses a probe that aspirates and discharges a sample, at least one pressure sensor that detects pressure inside a dispensing channel connecting a dispensing syringe which generates pressure for aspirating the sample from and discharging the sample to the probe, pressure value storage means for storing an output value of the pressure sensor during a dispensing operation of the sample as a time-series, storage means for storing a reference database having a time-series output value of the pressure sensor when the probe normally aspirates or discharges the sample, and an automatic analyzer that calculates a Mahalanobis distance from comparison data created based on the output value of the pressure sensor which is stored as a time-series by the pressure value storage means, and the reference database, and that determines abnormal dispensing of the sample by comparing the calculation result with a predetermined threshold value.

CITATION LIST

Patent Literature

PTL 1: JP-A-2008-224691

SUMMARY OF INVENTION

Technical Problem

However, the above-described related art has the following problem.

According to the automatic analyzer in the above-described related art, a reference is a time-series pressure data group created when dispensing is normally performed after the probe normally aspirates or discharges the sample. However, the output value of the pressure sensor receives the influence of variations in an inner diameter of a sample probe or a tube in a pressure measurable system, a length of the dispensing channel, and sensitivity of the pressure sensor. Consequently, if the variations are enormous, each device has a significant characteristic difference in the reference. As a result, there is a problem of inaccurately detecting the abnormal dispensing.

The invention is made in view of the above-described problem, and an object thereof is to provide an automatic analyzer which can more reliably detect abnormal dispensing in a dispensing mechanism.

Solution to Problem

In order to achieve the object, there is provided an automatic analyzer including: a dispensing mechanism that dips a dispensing nozzle in a dispensing target contained in a container, aspirates the dispensing target, and discharges the dispensing target to a reaction container; a pressure sensor that detects pressure inside the dispensing nozzle of the dispensing mechanism; a storage unit that stores multiple items of determination-purpose reference data used in determining whether or not the dispensing mechanism is abnormal; a determination-purpose reference data selection unit that selects one item of the determination-purpose reference data from the multiple items of the determination-purpose reference data stored in the storage unit, based on the detection result from the pressure sensor when the dispensing mechanism dispenses a reference dispensing target configured to contain a known ingredient; and an abnormality determination unit that determines whether or not the dispensing mechanism is abnormal, based on the detection result from the pressure sensor and the determination-purpose reference data when the dispensing mechanism dispenses a dispensing target used in analysis.

Advantageous Effects of Invention

According to the invention, it is possible to more reliably detect abnormal dispensing in a dispensing mechanism.

BRIEF DESCRIPTION OF DRAWINGS

FIG. 1 is a view briefly illustrating an overall configuration of an automatic analyzer according to an embodiment.

FIG. 2 is a view schematically illustrating an internal configuration of a sample dispensing mechanism as a representative of multiple dispensing mechanisms.

FIG. 3 is a functional block diagram illustrating details of a control device.

FIG. 4 is a table schematically illustrating an example of a group of known data.

FIG. 5 is a conceptual diagram illustrating a selection process of determination-purpose reference data which is performed by a determination-purpose reference data selection unit 95.

FIG. 6 is a graph illustrating an example of a relationship between comparison data and pressure waveform data when a reference dispensing target is aspirated.

FIG. 7 is a flowchart in the selection process of the determination-purpose reference data.

FIG. 8 is a flowchart illustrating an abnormality determination process.

FIG. 9 is a view illustrating a selection executing screen of the determination-purpose reference data, and is a view illustrating a state in which a selection button for a selection executing target is displayed.

FIG. 10 is a view illustrating the selection executing screen of the determination-purpose reference data, and is a view illustrating a state in which a comment regarding no need to change the determination-purpose reference data is displayed.

FIG. 11 is a view illustrating the selection executing screen of the determination-purpose reference data, and is a view illustrating a state in which the selection button for selecting whether to change the determination-purpose reference data or not is displayed.

DESCRIPTION OF EMBODIMENTS

An embodiment of the invention will be described with reference to the drawings.

(1) Overall Configuration of Automatic Analyzer

FIG. 1 is a view briefly illustrating an overall configuration of an automatic analyzer according to the present embodiment.

Referring to FIG. 1, the automatic analyzer is briefly configured to include a sample disk 10, a first reagent disk 20, a second reagent disk 30, a reaction disk 40, a sample dispensing mechanism 50, a first reagent dispensing mechanism 60, a second reagent dispensing mechanism 70, a photometric mechanism 80, and a control device 90.

The sample disk 10 has multiple specimen containers 11 which are mounted thereon side by side in the circumferential direction, and which contain a living body specimen (hereinafter, referred to as a specimen) such as blood or urine serving as an analysis target. The sample disk 10 is rotatably driven by a rotary driving device (not illustrated), and conveys the specimen containers 11 in the circumferential direction.

The first reagent disk 20 has multiple reagent containers 21 which are mounted thereon side by side in the circumferential direction, and which contain a reagent (first reagent) used in analyzing the specimen. The first reagent disk 20 is rotatably driven by a rotary driving device (not illustrated) in the circumferential direction, and conveys the reagent containers 21 in the circumferential direction.

The second reagent disk 30 has multiple reagent containers 31 which are mounted thereon side by side in the circumferential direction, and which contain a reagent (second reagent) used in analyzing the specimen. The second reagent disk 30 is rotatably driven by a rotary driving device (not illustrated) in the circumferential direction, and conveys the reagent containers 31 in the circumferential direction.

The reaction disk 40 has multiple reaction containers 41 which are mounted thereon side by side in the circumferential direction, and which contain a liquid mixture (reaction liquid) of the specimen and the reagent. The reaction disk 40 is rotatably driven by a rotary driving device (not illustrated) in the circumferential direction, and conveys the reaction containers 41 in the circumferential direction. In addition, a stirring mechanism 42 which stirs the liquid mixture contained in the reaction containers 41 and a cleaning mechanism 43 which cleans the reaction containers 41 whose analysis has been completed are arranged on a conveyance route of the reaction containers 41 of the reaction disk 40.

The sample dispensing mechanism 50 dips a dispensing nozzle 51 (refer to FIG. 2 below) into the dispensing target specimen contained in the specimen container 11. The sample dispensing mechanism 50 aspirates the specimen, and discharges the specimen to the reaction container 41, thereby dispensing the specimen. The sample dispensing mechanism 50 is driven in the horizontal direction and in the vertical direction by a drive mechanism (not illustrated).

The first reagent dispensing mechanism 60 dips a dispensing nozzle (not illustrated) into the first dispensing target reagent contained in the reagent container 21. The first reagent dispensing mechanism 60 aspirates the first reagent, and discharges the first reagent to the reaction container 41, thereby dispensing the first reagent. The first reagent dispensing mechanism 60 is driven in the horizontal direction and in the vertical direction by a drive mechanism (not illustrated).

The second reagent dispensing mechanism 70 dips a dispensing nozzle (not illustrated) into the second dispensing target reagent contained in the reagent container 31. The second reagent dispensing mechanism 70 aspirates the second reagent, and discharges the second reagent to the reaction container 41, thereby dispensing the second reagent. The second reagent dispensing mechanism 70 is driven in the horizontal direction and in the vertical direction by a drive mechanism (not illustrated).

The photometric mechanism. 80 is arranged on the conveyance route of the reaction container 41 in the reaction disk 40, and includes a light source 81 which emits light to the reaction container 41 containing a measurement target reaction liquid and a spectroscopic detector 82 which detects transmitted light transmitted through the reaction liquid contained in the reaction container 41. The detection result of the spectroscopic detector 82 is converted into a digital signal, and is sent to the control device 90.

The control device 90 controls the overall operation of the automatic analyzer including each drive mechanism, and controls an analysis process for analyzing the specimen such as blood or urine serving as the analysis target and an abnormality determination process for determining abnormality of the respective dispensing mechanisms 50, 60, and 70 in response to the analysis process. The control device 90 includes an input device 91 for inputting various setting values, instructions, or the like and a display device 92 for displaying various setting screens, analysis result screens or the like.

(1-1) Dispensing Mechanism 50, 60, and 70

FIG. 2 is a view schematically illustrating an internal configuration of a sample dispensing mechanism as a representative of multiple dispensing mechanisms.

As illustrated in FIG. 2, the sample dispensing mechanism 50 includes the dispensing nozzle 51 having a dispensing channel 53 through the inside of which a specimen 51$a$ and a system liquid 51$b$ pass, a metering pump 57 which aspirates and discharges the sample 51$a$, the system liquid 51$b$, separated air 51$c$ and the like with respect to the dispensing nozzle 51, a pressure sensor 54 which detects pressure inside the dispensing nozzle 51 (in other words, inside the dispensing channel 53), a pump 59 which is connected to the dispensing channel 53, and a valve 58 which is disposed in a channel between the dispensing channel 53 and the pump 59.

A throttle portion 52 whose cross-sectional area is small in the dispensing channel 53 is disposed in one end on a side of the dispensing nozzle 51 which is dipped in the reagent.

The metering pump 57 is connected to the other end of the dispensing nozzle 51. A drive mechanism 56 causes a plunger 55 to enter the inside of the dispensing channel 53, or causes the plunger 55 to retreat from the inside of the dispensing channel 53. In this manner, the metering pump 57 adjusts the capacity inside the dispensing channel 53, thereby aspirating and discharging the specimen or the like through the throttle portion 52.

The pump 59 supplies the system liquid 51$b$ to a dispensing route 53, and is controlled together with open and closed states of the valve 58 by the control device 90.

The detection result of the pressure sensor 54 is sent to the control device 90 via an A/D converter 54a.

The first and second reagent dispensing mechanisms 60 and 70 also have the same configuration as the sample dispensing mechanism 50, and thus detailed description thereof will be omitted.

(1-2) Control Device 90

FIG. 3 is a functional block diagram illustrating details of the control device.

Referring to FIG. 3, in addition to the input device 91 and the display device 92, the control device 90 includes various functional blocks such as a pressure signal processing unit 97 that calculates feature variables in a digital pressure signal from the A/D converter 54a in the respective dispensing mechanisms 50, 60, and 70, a storage unit 93 that stores various information items used in operations of the automatic analyzer such as the analysis process or the abnormality determination process, a statistic distance calculation unit 94 that calculates a statistic distance which is an index obtained by quantifying similarity between two events represented by multiple feature variables, a determination-purpose reference data selection unit 95 that selects one item of determination-purpose reference data used in the actual abnormality determination process of the dispensing process from multiple items of determination-purpose reference data stored in the storage unit 93 in order to be used in the abnormality determination process of the dispensing process, and an abnormal dispensing process determination unit 96 that performs the abnormality determination process of the dispensing process by using the determination-purpose reference data selected by the determination-purpose reference data selection unit 95.

(2) Analysis Process

A basic operation in an analysis process of the automatic analyzer according to the present embodiment will be described.

In the analysis process, qualitative/quantitative analysis is performed by adding a reagent specifically reacting to a specific ingredient contained in the specimen such as blood or urine, by causing the reagent to react therewith, and by measuring optical density of the reaction liquid.

First, an analysis target specimen (sample) is placed in the specimen container 11, and the specimen container 11 is mounted on the sample disk 10. Information (items to be analyzed, types of reagents, or the like) required for the analysis process of each specimen is input through the input device 91 and is stored in the control device 90 in advance.

Next, a certain amount of a specimen is aspirated from the specimen container 11 by using the dispensing probe 51 of the sample dispensing mechanism 50, and is discharged to the reaction container 41 mounted on the reaction disk 40, thereby performing dispensing.

Subsequently, a predetermined amount of reagent is aspirated from the reagent containers 21 and 31 by using the first and second reagent dispensing mechanisms 60 and 70, and is discharged to the reaction container 41 of the reaction disk 40, thereby performing dispensing and causing the stirring mechanism 42 to performing stirring. A type, amount, timing or the like of the reagent to be dispensed by the first and second reagent dispensing mechanisms 60 and 70 is determined in advance depending on type, items or the like to be analyzed in the specimen.

Subsequently, the reaction disk 40 is periodically and repeatedly rotated and stopped. Photometry is performed at a timing when the reaction container 41 passes the photometric mechanism 80 (that is, between the light source 81 and the spectroscopic detector 82). The photometry is repeatedly performed by the spectroscopic detector 82 during a predetermined reaction time period. Thereafter, the cleaning mechanism 43 cleans the reaction container 41 which completes the analysis. The photometry is also performed on the multiple specimen containers 41 in parallel by the photometric mechanism 80. The detection result obtained by the photometric mechanism 80 is sent to the control device 90, concentration of the ingredient is calculated depending on the type of the analysis, and is displayed on the display device 91.

(2-1) Dispensing Process

A basic operation of the dispensing operation performed by the dispensing mechanism in the analysis process will be described.

Herein, the sample dispensing mechanism 50 will be described as a representative of the dispensing mechanisms 50, 60, and 70.

In the dispensing process (that is, dispensing process of the specimen) performed by the sample dispensing mechanism 50, in a state in which the dispensing probe 51 is dipped in the specimen which is a dispensing target, the specimen is aspirated and discharged to the predetermined reaction container 41, thereby performing the dispensing.

Before the specimen is aspirated, the control device 90 first opens the valve 58, fills the inside of the dispensing channel 53 of the dispensing probe 51 with the system liquid 51b supplied from the pump 59, and closes the valve 58. Then, in a state in which a distal end of the dispensing probe 51 is located in the air, the drive mechanism 56 operates the plunger 55 to be lowered, and the separated air 51c is aspirated.

Next, the dispensing probe 51 is lowered into the specimen container 11. In a state in which the distal end is dipped in the specimen, the plunger 55 is operated again and lowered. The specimen is aspirated into the throttle portion 52 and the dispensing channel 53 of the dispensing probe 51. Thereafter, in a state in which the dispensing probe 51 is moved onto the reaction container 41, the drive mechanism 56 operates the plunger 55 to be raised, and the specimen is aspirated until the specimen reaches the separated air 51c.

Pressure in the dispensing channel 53 of the dispensing probe 51 when the dispensing probe 51 aspirates and discharges the specimen is detected by the pressure sensor 54. The pressure is converted into a digital signal by the A/D converter 54a, and the digital signal is sent to the control device 90. The control device 90 performs an abnormality determination process for determining whether or not the respective dispensing mechanisms 50, 60, and 70 are abnormal, based on the detection result of the pressure sensor 54 (that is, a pressure waveform during the aspirating and the discharging). If it is determined that there is an abnormality, the analysis process is temporarily stopped, which causes the display device 92 to display a warning and the like. In this manner, an operator is notified of the warning and can then initiate a recovery operation. As the recovery operation, any one among re-dispensing after removing the cause of the abnormality, performing analysis on another specimen, stopping the device, and the like may be selected.

After discharging the specimen, the dispensing probe 51 is cleaned with the system liquid 51b flowing in response to opening and closing of the valve 58, and is provided for the subsequent dispensing process.

(2-2) Abnormality Determination Process

The abnormality determination process is a process for determining whether the respective dispensing mechanisms 50, 60, and 70 are abnormal during the dispensing process.

In the abnormality determination process, the statistic distance calculation unit 94 acquires a pressure waveform (that is, the detection result of the pressure sensor 54) when each of the dispensing nozzles of the respective dispensing mechanisms 50, 60, and 70 aspirates and discharges a target (specimen or reagent), acquires determination-purpose reference data selected by the determination-purpose reference data selection unit 95 from multiple items of determination-purpose reference data stored in the storage unit 93, and calculates a statistic distance therebetween. In the present embodiment, a case where a Mahalanobis distance is employed as the statistic distance used in the statistic distance calculation unit 94 will be described as an example.

The abnormal dispensing determination unit 95 compares the statistic distance calculated by the statistic distance calculation unit 94 with a threshold value stored in the storage unit 93, and determines abnormal dispensing of the respective dispensing mechanisms 50, 60, and 70, based on the comparison result. The threshold value stored in the storage unit 93 is determined in advance depending on each dispensing process target and each dispensing amount.

(2-2.1) Statistic Distance

The statistic distance is an index obtained by quantifying similarity between two events represented by multiple feature variables. In the case of the present embodiment, calculation is performed based on how far target data is away from a group of items of known data prepared in advance. Herein, a calculation method of the Mahalanobis distance will be described as an example of the statistic distance.

FIG. 4 is a table schematically illustrating an example of a group of items of the known data. In the group of the items of known data, each item of data of n number of events has k number of feature variables (n and k are positive integers).

In order to calculate the Mahalanobis distance, normalization is first performed by using (Equation 1) below, when the respective feature variables of the target data are set to $y_1, y_2, \ldots, y_k$, average values of the respective feature variables of known data $x_{nk}$ are set to $z_1, z_2, \ldots, z_k$, and standard deviations are set to $\sigma_1, \sigma_2, \ldots, \sigma_k$.

[Expression 1]

$$X_i = \frac{y_i - z_i}{\sigma_i} \quad \text{(Equation 1)}$$

However, a condition is set such that i=1, . . . , k.

Then, a Mahalanobis distance $D_M$ of the target data from the group of the known data is expressed by (Equation 2) below.

[Expression 2]

$$D_M = \sqrt{\frac{1}{k}(X_1 \cdots X_k)A\begin{pmatrix}X_1 \\ \vdots \\ X_k\end{pmatrix}} \quad \text{(Equation 2)}$$

In addition to the Mahalanobis distance, the calculation method of the statistic distance which can be applied to the present embodiment includes a calculation method of a Euclidean distance, a standard Euclidean distance, a Manhattan distance, a Chebychev distance, or a Minkowski distance, and multivariate normal density.

(2-2.2) Selection of Determination-Purpose Reference Data

The determination-purpose reference data used in the abnormality determination process is selected from multiple items of the determination-purpose reference data stored in the storage unit 93.

FIG. 5 is a conceptual diagram illustrating a selection process of the determination-purpose reference data which is performed by the determination-purpose reference data selection unit 95. In addition, FIG. 6 is a graph illustrating an example of a relationship between a certain item of the comparison data (equivalent to the group of the known data) and pressure waveform data (equivalent to the target data) when a reference dispensing target is aspirated. The determination-purpose reference data used in the dispensing abnormality determination process is selected independently from a normal analysis operation before the automatic analyzer starts the analysis process.

The storage unit 93 stores multiple items of the determination-purpose reference data related to the respective dispensing mechanisms 50, 60, and 70. The comparison data for use in selection is associated with and stored in each item of the determination-purpose reference data. First, the respective dispensing mechanisms 50, 60, and 70 aspirate and discharge a predetermined reference dispensing target (for example, purified water, air, or the like) so as to acquire pressure data. The statistic distance is calculated based on the comparison data of the pressure data. Then, the determination-purpose reference data associated with the comparison data in which the statistic distance is shortest is selected as the determination-purpose reference data used in the abnormality determination process. The determination-purpose reference data is selected for the respective dispensing mechanisms 50, 60, and 70 depending on each dispensing amount.

The comparison data is pressure signal data when a fluid (reference dispensing target) serving as a reference such as purified water or air is aspirated and discharged in a device under conditions in which variations are reproduced within a normally probable range such as in relation to the inner diameter of the probe. That is, the comparison data is obtained by reproducing a characteristic difference of the device.

The reference determination-purpose data is pressure signal data acquired in view of portions other than the characteristic difference of the device which affects the pressure waveform such as the viscosity, syringe operation pattern, amount of the sample dispensed in a device under conditions in which each item of comparison data is acquired. A threshold value of the dispensing abnormality determination process which is common to each item of determination-purpose reference data is set.

For example, as illustrated in FIG. 5, it is assumed that comparison data items A, B, and C are associated with the respective multiple (for example, three) determination-purpose reference data items 1, 2, and 3 stored in the storage unit 93. If the statistic distances from the respective comparison data items A, B, and C of the pressure signal when the reference dispensing target is aspirated and discharged are respectively 9, 6, and 3, the shortest statistic distance relates to the comparison data item C. Accordingly, the determination-purpose reference data item 3 associated with the comparison data item C is selected so as to be used in the abnormality determination process.

FIG. 7 is a flowchart illustrating the selection process of the determination-purpose reference data.

First, the control device 90 causes any one of the sample dispensing mechanism 50, the first reagent dispensing mechanism 60, and the second reagent dispensing mechanism 70 to aspirate and discharge the reference dispensing target (Step S10). The pressure signal processing unit 97 of the control device 90 calculates the feature variables, based on the digital signal of the pressure waveform which is sent from the A/D converter 54a (Step S20). The statistic distance $D_M$ between the calculated feature variables and the respective multiple comparison data items held in advance is calculated (Step S30). The determination-purpose reference data combined with the comparison data in which the statistic distance $D_M$ is shortest is selected so as to be used in the dispensing abnormality determination process (Step S40).

According to the present embodiment, the determination-purpose reference data to be used in the abnormality determination process is selected, based on the calculated statistic distance. However, it is also conceivable that the threshold value for use in the dispensing abnormality determination process is corrected or the threshold value is selected from multiple threshold values, based on the calculated statistic distance.

According to the present embodiment, in order to acquire the comparison data to be used in calculating the statistic distance (Mahalanobis distance), purified water, air, or the like is aspirated and discharged in advance so as to acquire the pressure signal waveform having the n number of events, and the k number of feature variables which express the waveform pattern are extracted from each pressure signal waveform. In this case, the feature variables include an average pressure value at every constant interval of time, or a timing at which a minimum point and a maximum point appear in pressure fluctuations when the plunger 55 starts and stops operating. As an average deviation and standard deviation of the respective feature variables, and an inverse matrix of a correlation matrix, multiple types thereof are stored in advance in the storage unit 93.

(2-2.3) Operation of Abnormality Determination Process

FIG. 8 is a flowchart illustrating the abnormality determination process.

Referring to FIG. 8, an operation of the sample dispensing mechanism 50 will be described as an example. However, the first reagent dispensing mechanism 60 and the second reagent dispensing mechanism 70 also similarly perform the abnormality determination process.

When receiving the instruction to start the analysis, the control device 90 causes the sample dispensing mechanism 50 to perform the aspirating operation in the dispensing step (Step S100), and causes the pressure signal processing unit 97 to calculate the feature variables of the target data, based on the digital signal of the pressure waveform which is sent from the A/D converter 54a (Step S200). Subsequently, the statistic distance calculation unit 94 calculates the statistic distance $D_M$ from the determination-purpose reference data selected in advance from the target data (Step S300). Then, the control device 90 causes the abnormal dispensing process determination unit 96 to determine whether or not the statistic distance $D_M$ is smaller than the predetermined threshold value (Step S400). If the determination result in Step S400 is NO, a recovery process is performed (Step S410), thereby completing the process. The recovery process is a process in which the abnormal dispensing process determination unit 96 issues information indicating that the aspirating is abnormal, and the control device 90 sends a warning and an operation to process another specimen.

In addition, if the determination result in Step S400 is YES, the discharging operation is performed (Step S500), and it is determined whether or not the subsequent dispensing occurs (Step S600). If the determination result is YES, that is, if the subsequent dispensing occurs, the process returns to the process in step S100. If the determination result is NO, that is, if the subsequent dispensing does not occur, the process is completed.

Herein, the process is also similarly performed for the pressure fluctuations during the discharging.

(2-2.4) Display Process

FIG. 9 is a view illustrating a display example of an executing screen for selecting the determination-purpose reference data in the display device 92 of the control device 90.

Referring to FIG. 9, an executing screen 921 for selecting the determination-purpose reference data has selection buttons 921a, 921b, and 921c arranged therein in order to select which dispensing system (dispensing mechanisms 50, 60, and 70) of the sample, the first reagent, and the second reagent is used when selecting the determination-purpose reference data used in the dispensing abnormality determination process. An operator selects the selection buttons 921a, 921b, and 921c by using a graphical user interface (GUI, not illustrated) or the like, thereby selecting which dispensing system (dispensing mechanisms 50, 60, and 70) is used. For example, the determination-purpose reference data used in the dispensing abnormality determination process is selected when the device is installed or components related to the dispensing channel such as the probe are replaced. The determination-purpose reference data is periodically selected, thereby enabling the operator to detect an abnormal dispensing channel.

FIG. 10 illustrates a case where the dispensing system which is the selection target of the determination-purpose reference data is selected on the executing screen 921 for selecting the determination-purpose reference data, and as a result, FIG. 10 illustrates a case of displaying a comment 921d indicating that it is not necessary to change the determination-purpose reference data currently used by the selected dispensing system.

FIG. 11 illustrates a case where the dispensing system which is the selection target of the determination-purpose reference data is selected on the executing screen 921 for selecting the determination-purpose reference data, and as a result, FIG. 11 illustrates a case of displaying a comment 921e indicating that it is recommendable to change the determination-purpose reference data currently used by the selected dispensing system and checking whether to change the determination-purpose reference data, a YES button 921f for instructing changing of the determination-purpose reference data, and a NO button 921g for instructing not to change the determination-purpose reference data. When it is determined that it is necessary to change the determination-purpose reference data regardless of whether the components related to the dispensing channel are not replaced, an operator can recognize that there is a possibility that the dispensing channel system may be abnormal.

(3) Advantageous Effect of Present Embodiment

An advantageous effect of the present embodiment configured as described above will be described.

According to the automatic analyzer in the related art, a reference is a time-series pressure data group created when the dispensing is normally performed after the probe normally aspirates or discharges the sample. However, the output value of the pressure sensor receives the influence of variations in the inner diameter of the sample probe or the tube in the pressure measurable system, the length of the dispensing channel, and sensitivity of the pressure sensor. Consequently, if the variations are enormous, each device has a significant characteristic difference in the reference. As a result, there is a problem of inaccurately detecting the abnormal dispensing.

In contrast, according to the present embodiment, a configuration is adopted in which the multiple items of determination-purpose reference data used in determining whether or not the dispensing mechanism is abnormal are stored, in which one item of determination-purpose reference data is selected from the multiple stored items of determination-purpose reference data, based on the detection result from the pressure sensor when the dispensing mechanism dispenses the reference dispensing target configured to contain the known ingredient, and in which it is determined whether or not the dispensing mechanism is abnormal, based on the detection result from the power sensor and the determination-purpose reference data when the dispensing mechanism dispenses the dispensing target used in the analysis. Accordingly, it is possible to more reliably detect the abnormal dispensing in the dispensing mechanism. That is, without being affected by the characteristic differences in each device, it is possible to reliably detect the abnormal dispensing caused by various factors. Therefore, it is possible to obtain very reliable analysis results.

For example, when a test sample or the reagent is dispensed, various factors may cause the abnormal dispensing to occur. The factors which may cause the abnormal dispensing of the sample include clogging of the probe which is frequently caused by aspirating solid substances such as fibrin. If the clogging occurs in the probe, a predetermined amount of a sample cannot be dispensed to the reaction container, and thus it is not possible to obtain reliable analysis results. In addition, even when air bubbles or liquid films are present on the surface of the liquid test sample, abnormal dispensing may occur. If the amount by which the probe is dipped in the test sample increases, contamination increases, thereby causing a possibility that the analysis results may be adversely affected. Therefore, in order to minimize the depth by which the probe is dipped in the liquid as much as possible, a technique is generally employed which controls an operation so as to aspirate a predetermined amount of liquid into the probe by detecting the liquid surface of the liquid inside the container, and by stopping the lowering operation of the probe at a position where the distal end of the probe reaches slightly below the liquid surface. As means for detecting the surface of the liquid test sample, a generally used technique is an electrostatic capacity change method for detecting a change in electrostatic capacity when the probe comes into contact with the liquid surface. When this liquid surface sensor is used, if air bubbles or a film are present on the liquid surface which is a detecting target, in some cases, the air bubbles or the film are erroneously detected as the liquid surface, thereby leading to the abnormal dispensing. This case also occurs even when the reagent is dispensed. Consequently, the bubbles generated inside the reagent container cause the abnormal dispensing to occur, in some cases.

According to the present embodiment, with regard to this problem, it is also possible to more reliably detect the abnormal dispensing of the dispensing mechanism.

REFERENCE SIGNS LIST

10 SAMPLE DISK
11 SPECIMEN CONTAINER
12 SPECIMEN CONTAINER RACK
20 FIRST REAGENT DISK
21 REAGENT CONTAINER
30 SECOND REAGENT DISK
31 REACTION CONTAINER
40 REACTION DISK
41 REACTION CONTAINER
42 STIRRING MECHANISM
43 CLEANING MECHANISM
50 SAMPLE DISPENSING MECHANISM
51 DISPENSING NOZZLE
52 THROTTLE PORTION
53 DISPENSING CHANNEL
54 PRESSURE SENSOR
55 PLUNGER
56 DRIVE MECHANISM
57 METERING PUMP
58 VALVE
59 PUMP
60 FIRST REAGENT DISPENSING MECHANISM
70 SECOND REAGENT DISPENSING MECHANISM
80 PHOTOMETRIC MECHANISM
90 CONTROL DEVICE
91 INPUT DEVICE
92 DISPLAY DEVICE
93 STORAGE UNIT
94 STATISTIC DISTANCE CALCULATION UNIT
95 DETERMINATION-PURPOSE REFERENCE DATA SELECTION UNIT
96 ABNORMAL DISPENSING PROCESS DETERMINATION UNIT

The invention claimed is:

1. An automatic analyzer comprising:
a dispensing mechanism including a dispensing nozzle;
a plurality of containers;
a plurality of reaction containers;
a photometric mechanism configured to emit light and detect light that has been transmitted through a reaction container containing a solution, of the plurality of reaction containers;
a pressure sensor that detects pressure inside the dispensing nozzle of the dispensing mechanism;
a storage unit that stores multiple items of reference data that are respectively associated with multiple items of comparison data, the comparison data is pressure data related to a known ingredient within a reference dispensing target;
a controller connected to the dispensing mechanism, the photometric mechanism, the pressure sensor, and the storage unit, the controller programmed to:
control the dispensing mechanism to dip a portion of the dispensing nozzle into the reference dispensing target having the known ingredient contained in a first container of the plurality of containers, aspirate the reference dispensing target, and discharge the reference dispensing target into a first reaction container of the plurality of reaction containers, and control the pressure sensor to detect a pressure inside the dispensing nozzle to obtain a first detection result,
calculate multiple first statistical distances between respective multiple items of comparison data stored in the storage unit and the first detection result from the pressure sensor, and select one item of the reference data, from the multiple items of the reference data stored in the storage unit, that is associated with an item of comparison data, of the multiple items of comparison data, that has a shortest calculated first statistical distance between the multiple items of comparison data and the first detection result, control the dispensing mechanism to dip a portion of the dispensing nozzle into a biological sample target contained in a second container of the plurality of containers, aspirate the biological sample target, and discharge the biological sample target into a second reaction container of the plurality of reaction containers, and control the pressure sensor to detect a pressure inside the dispensing nozzle to obtain a second detection result, calculate a second statistical distance between the selected item of reference data and the second detection result from the pressure sensor and determine whether there is an abnormality of discharging the biological sample target based on whether the second statistical distance is less than or equal to a predetermined threshold value.

2. The automatic analyzer according to claim 1, wherein the storage unit stores the multiple items of the reference data in a one to one correspondence in advance with the respective multiple items of the comparison data.

3. The automatic analyzer according to claim 1, wherein the statistical distance is any one of a Mahalanobis distance, a Euclidean distance, a standard Euclidean distance, a Manhattan distance, a Chebychev distance, or a Minkowski distance, and multivariate normal density.

\* \* \* \* \*